United States Patent [19]

Schacht et al.

[11] 4,051,170
[45] Sept. 27, 1977

[54] DIPHENOXYACETIC ACID DERIVATIVES

[75] Inventors: Erich Schacht; Werner Mehrhof; Zdenek Simane; Detlev Kayser; Herbert Nowak, all of Darmstadt, Germany

[73] Assignee: Merck Patent Gesellschaft mit beschrankter Haftung, Darmstadt, Germany

[21] Appl. No.: 531,475

[22] Filed: Dec. 11, 1974

[30] Foreign Application Priority Data

Dec. 15, 1973 Germany .............................. 2362416

[51] Int. Cl.² .......................................... C07G 69/76
[52] U.S. Cl. ........................ 560/62; 260/287 R; 260/293.82; 260/293.83; 260/327 R; 260/345.5; 260/520 C; 260/501.7; 260/501.2; 424/258; 424/267; 424/289
[58] Field of Search ....................... 260/520 C, 473 G

[56] References Cited

U.S. PATENT DOCUMENTS

| 3,454,581 | 7/1969 | Groit | 260/520 C |
| 3,474,128 | 10/1969 | Griot | 260/520 C |
| 3,517,051 | 6/1970 | Bolhofer | 260/520 C |
| 3,526,632 | 9/1970 | Griot | 260/473 G |
| 3,546,229 | 12/1970 | Groit | 260/520 C |
| 3,681,365 | 8/1972 | Griot | 260/473 G |
| 3,707,549 | 12/1972 | Mills | 260/520 C |

Primary Examiner—Paul J. Killos
Attorney, Agent, or Firm—Millen & White

[57] ABSTRACT

Diphenoxyacetic acid derivatives of the general formula

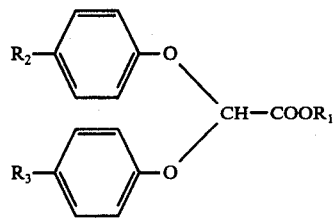

wherein $R_1$ is H or alkyl of 1-4 carbon atoms, $R_2$ is H or Cl, $R_2$ is H or Cl, $R_3$ is piperidino, 4-piperidinophenyl, 1,2,3,4-tetrahydroquinolino, 1-$R_4$-1,2,3,4-tetrahydro-4-quinolyl, 4-oxo-1,2,3,4-tetrahydroquinolino, 4-chromanyl, 4-thiochromanyl or 4-chlorophenoxy, and $R_4$ is H or alkyl of 1-4 carbon atoms, and the physiologically acceptable salts thereof, possess cholesterol level lowering activity and can be prepared by reacting a phenol of the formula

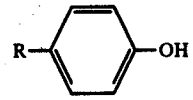

with a compound of the formula

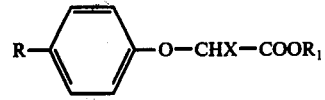

wherein X is OH, esterified OH, Cl, Br or I, one R is $R_2$ and the other is $R_3$; or by cyclizing a compound of the formula

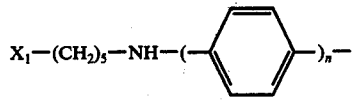

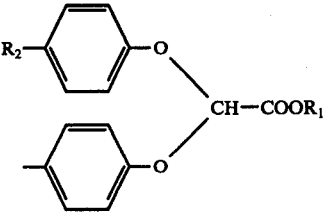

wherein $X_1$ is Cl, Br, I, $NH_2$, OH or an esterified or etherified OH-group and $n$ is 0 or 1; or by treating a compound of the formula

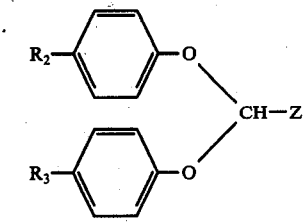

wherein Z is a functionally modified carboxyl group different from $COOR_1$, with a solvolyzing agent, $R_1$, $R_2$ and $R_3$ in each instance having the values given above.

5 Claims, No Drawings

DIPHENOXYACETIC ACID DERIVATIVES

BACKGROUND OF THE INVENTION

This invention relates to novel diphenoxyacetic acid derivatives.

U.S. Pat. No. 3,681,385 discloses diphenoxyacetic acid derivatives wherein the phenyl groups have as p-substituents H, Cl, Br, I, $CF_3$ or phenyl. See also the references cited therein. U.S. Pat. No. 3,804,839 discloses 2-p-(heterocyclic ring)- and p-(2-indanyl)-phenoxy-2-methyl-propionic acids and alkyl esters thereof having cholesterol and triglyceride blood level lowering activity. Nakamura et al., Chem. Abstracts 75, 151545 (1971), discloses corresponding compounds wherein the p-substituent on the phenyl ring is cycloalkenyl, benzothiazolyl or benzoxazolyl. Dujovne et al., Chem. Abstracts, 74, 75049, discloses corresponding compounds wherein the p-substituent is tetrahydronaphthyl, (nafenopin) or chloro (clofibrate), as having cholesterol and triglyceride blood level lowering activity. The p-substituent on the phenoxy substituent of the compounds of this invention is phenoxymethyl or halophenoxymethyl. See also U.S. Pat. No. 3,563,998. Heterocyclic p-substituted phenoxy acetic and propionic acids are the subject of prior filed Applications Ser. No. 122 449,332, filed Mar. 8, 1974 now U.S. Pat. No. 3,992,386 and Ser. No. 127 497,300, filed Aug. 14, 1974 now U.S. Pat. No. 3,968,143.

SUMMARY OF THE INVENTION

In a composition aspect, this invention relates to diphenoxyacetic acid derivatives of the general Formula I

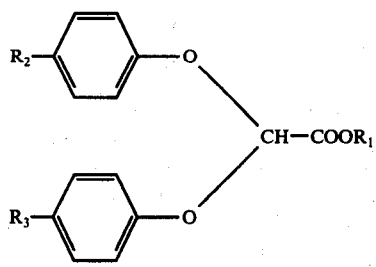

I wherein $R_1$ is H or alkyl of 1-4 carbon atoms; $R_2$ is H or Cl; $R_3$ is piperidino, 4-piperidinophenyl, 1,2,3,4-tetrahydroquinolino, 1-$R_4$-1,2,3,4-tetrahydro-4-quinolyl, 4-oxo-1,2,3,4-tetrahydroquinolino, 4-chromanyl, 4-thiochromanyl or 4-chlorophenoxy; and $R_4$ is H or alkyl of 1-4 carbon atoms, and the physiologically acceptable salts thereof with acids or bases.

In another composition aspect, this invention relates to pharmaceutical compositions comprising at least one compound in admixture with a pharmaceutically acceptable carrier.

In process aspects, this invention relates to processes for producing compounds of Formula I and for using them for lowering cholesterol blood serum levels.

DETAILED DISCUSSION

Compounds of Formula I and the salts thereof possess, with good compatibility, excellent cholesterol blood serum level-lowering activity. They also possess triglyceride-level-lowering, uric-acid-level-lowering, and liver-enzyme-inducing activities.

The lowering of the cholesterol level can be determined, for example, in the serum of rats according to the method of Levine et al. Automation in Analytical Chemistry, Technicon Symposium 1967, Mediad, New York, pages 25-28. The lowering of the triglyceride level can likewise be evaluated in the rat serum according to the method of Noble and Campbell. Clin. Chem. 16 (1970), pp. 166-170. A manifestation of the liver enzyme induction can be seen, for example, in the increase of the liver weight after several days of administering one of the compounds to rats, as well as in a rise in the enzyme activities of the endoplasmic reticulum and other cellular structures in the rat liver.

The compounds of Formula I nd the physiologically acceptable salts thereof can be employed as medicinal agents and also as intermediates for the preparation of other medicines.

In the formulae hereinbelow, $R_1$ through $R_4$ have the meanings given for Formula I, unless expressly noted otherwise.

In the compounds of Formula I, alkyl is preferably methyl or ethyl. Other examples are n-propyl, isopropyl, n-butyl, isobutyl, sec.-butyl or tert.-butyl.

$R_1$ is preferably H, methyl or ethyl. $R_2$ is preferably Cl, $R_3$ is preferably 1,2,3,4-tetrahydro-4-quinolino or 1-methyl-1,2,3,4-tetrahydro-4-quinolyl, i.e., $R_4$ is preferably H or methyl.

Especially preferred are those compounds of Formula I wherein at least one of $R_1$, $R_2$, $R_3$ and $R_4$ has one of the above preferred values.

Several preferred classes of compounds are those of partial Formulae Ia through Ik, which otherwise correspond to Formula I, i.e., if $R_1$, $R_2$, $R_3$ or $R_4$ is not given a different value, it has the values given for Formula I, but wherein:

Ia—$R_1$ is H, methyl or ethyl;
Ib—$R_2$ is Cl;
Ic—$R_3$ is piperidino or 4-piperidinophenyl;
Id—$R_3$ is 1,2,3,4-tetrahydroquinolino, 1-$R_4$-1,2,3,4-tetrahydro-4-quinolyl or 4-oxo-1,2,3,4-tetrahydroquinolino;
Ie—$R_3$ is 1,2,3,4-tetrahydroquinolino or 1-methyl-1,2,3,4-tetrahydro-4-quinolyl;
If—$R_3$ is chromanyl;
Ig—$R_3$ is 4-thiochromanyl;
Ih—$R_3$ is 4-chlorophenoxy;
Ii—$R_4$ is H or methyl;
Ij—$R_1$ is H, methyl or ethyl, and $R_2$ is Cl;
Ik—$R_1$ is H, methyl or ethyl, $R_2$ is Cl and $R_3$ is 1,2,3,4-tetrahydroquinolino or 1-methyl-1,2,3,4-tetrahydro-4-quinolyl.

In a process aspect, this invention relates to a process for the preparation of diphenoxyacetic acid derivatives of general Formula I and the physiologically acceptable salts thereof with acids or bases, which comprises
a. reacting a phenol of Formula IIa

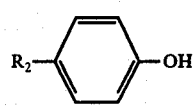

IIa or a reactive functional derivative thereof with a compound of Formula IIIa

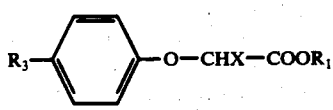

or reacting a phenol of Formula IIb

or a reactive functional derivative thereof with a compound of Formula IIIb

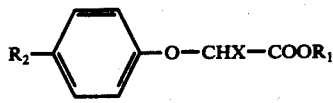

wherein X is OH, esterified OH, Cl, Br or I, or b. treating a compound of Formula IV

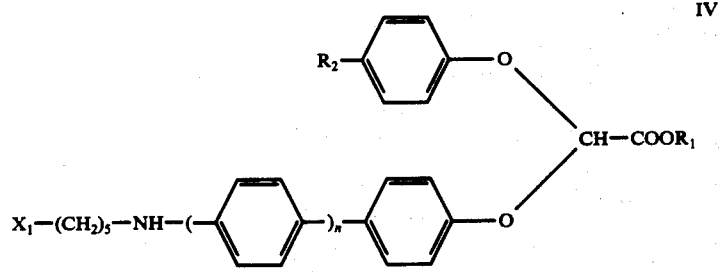

wherein $X_1$ is Cl, Br, I, $NH_2$, OH or an esterified or etherified OH-group, and n is 0 or 1, with a cyclizing agent; or c. treating a compound of Formula V

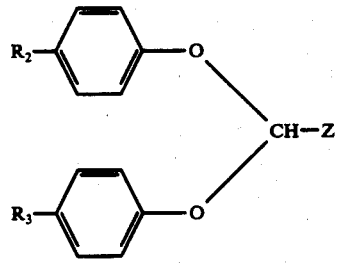

wherein Z is a functionally modified carboxyl group different from $COOR_1$, with a solvolyzing agent; and optionally thereafter converting, in a thus-obtained compound of Formula I, an $R_1$ group into another $R_1$ group by treatment with esterifying, interesterifying or solvolyzing agents, and/or converting a thus-produced compound of Formula I by treatment with an acid and/or a base into one of the physiologically acceptable salts thereof, and/or liberating a compound of Formula I from one of the salts thereof by treatment with a base or an acid, respectively.

In the above formulae, X and $X_1$ preferably are Cl or Br but, in addition to free OH and I, can also be, for example, alkylsulfonyloxy of especially 1-6 carbon atoms (e.g., methanesulfonyloxy), arylsulfonyloxy, preferably of 6-10 carbon atoms (e.g., benzenesulfonyloxy, p-toluenesulfonyloxy, 1- or 2-naphthalenesulfonyloxy) or acyloxy, preferably of 1-7 carbon atoms (e.g., acetoxy or benzoyloxy). Moreover, $X_1$ can also be $NH_2$ or, for example, an etherified OH-group, especially of 1-7 carbon atoms (e.g., methoxy, benzyloxy).

The diphenoxyacetic acid derivatives of Formula I can be prepared according to conventional methods described in the literature, preferably by reacting the phenols of Formula IIa or IIb with the compounds of Formula IIIa or IIIb, respectively. The phenols IIa are known and some of the phenols IIb are known. The later novel compounds can be produced according to conventional methods, e.g., by splitting their methyl ethers (corresponding to Formula IIb but having an $OCH_3$ group instead of OH) with HBr. Compounds of Formulae IIIa nd IIIb, respectively, are for the most part known. They can be obtained according to conventional methods. The phenol IIa or IIb can be converted, prior to the reaction, into a salt, especially a metallic salt, e.g., an alkali metal salt, preferably a Li, Na or K salt. For purposes of the salt formation, the phenol can be reacted with a reagent forming metallic salts, for example, an alkali metal, e.g., Na, an alkali metal hydride or amide, e.g., LiH, NaH, $NaNH_2$ or $KNH_2$, a lower alkali metal alcoholate, e.g., lithium, sodium, or potassium methylate, ethylate or tert.-butylate, an organometallic compound, e.g., butyllithium phenyllithium or phenyl-sodium, a metal hydroxide, carbonate or bicarbonate, e.g., lithium, sodium, potassium or calcium hydroxide, carbonate or bicarbonate. The phenolate is advantageously produced in the presence of a solvent, e.g., a hydrocarbon, e.g., hexane, benzene, toluene or xylene; an ether, e.g., diethyl ether, diisopropyl ether, tetrahydrofuran (THF), dioxane or diethylene glycol dimethyl ether; and amide, such as dimethylformamide (DMF) or hexamethylphosphoric triamide (HMPA); and alcohol, such as methanol or ethanol; a ketone, such as acetone or butanone; or a solvent mixture. The phenol IIa or IIb and/or a salt thereof is preferably reacted with a compound of Formula IIIa or IIIb, respectively, in the presence of a diluent, e.g., the solvent utilized for the preparation of the salt, which, however, can be replaced by another solvent or diluted with such other solvent.

The reaction is normally carried out at temperatures of −20° to 150°, preferably 20° to 120°, especially advantageously at the boiling temperature of the solvent. The reaction can be conducted under an inert gas, e.g., nitrogen. The phenolate can also be formed in situ, in which case the phenol and compound IIIa or IIIb are allowed to react with each other in the presence of the salt-forming reagent.

In an especially preferred method, the compounds IIa and IIa or IIb and IIIb (X = Cl or Br, $R_1$ = $CH_3$ or $C_2H_5$) are refluxed together with an alcoholic, e.g., ethanolic, sodium alcoholate solution for 2-8 hours.

It is also possible to react a free phenol IIa or IIb with a hydroxy acid derivative IIIa or IIIb (X = OH), respectively, preferably in the presence of a condensation agent. Suitable condensation agents are, for example, acidic dehydration catalysts, for instance mineral acids, such as sulfuric acid or phosphoric acid, as well as p-toluenesulfonyl chloride, arsenic acid, boric acid, $NaHSO_4$ and $KHSO_4$, and diaryl carbonates (e.g., diphenyl carbonate), dialkyl carbonates (e.g., dimethyl or diethyl carbonate) or carbondiimides (e.g., dicyclohexylcarbodiimide). If an acid is used as a condensation agent, the reaction is suitably carried out in an excess of this acid without adding a further solvent, at temperatures of about 0° to about 100°, preferably 50° to 60°. However, it is also possible to add diluents, e.g., benzene, toluene or dioxane. With the use of a carbonic acid ester, the reaction is advantageously conducted at an elevated temperature, suitably about 100° to about 210°, especially 180° to 200°, and in this case an interesterification catalyst can optionally be added, such as sodium or potassium carbonate or sodium methylate.

Compounds of Formula IV can be cyclized according to methods described in the literature to obtain compounds of Formula I, for example by heating in the presence or absence of a solvent, optionally in the presence of an acidic or basic catalyst.

Compounds of Formula IV are obtainable, for example, by reacting a compound of the formula $X_1$—$(CH_2)_5$—$X_1$ (wherein $X_1$ has the values given above, but the two groups $X_1$ can be identical or different and can also collectively represent O or NH, preferably 1,5-dibromopentane, but also, for example, 1,5-dichloro- or 1,5-diiodopentane, piperidine, 1,5-pentanediol and the reactive esters thereof, e.g., the bis-p-toluene-sulfonate thereof) with a compound of Formula VI

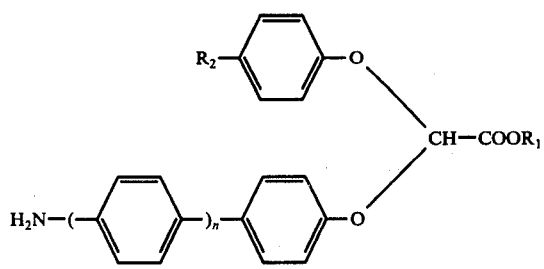

VI wherein $R_1$, $R_2$ and $n$ have the values given above. Suitable for the cyclization of IV are, for example, water, lower aliphatic alcohols, e.g., methanol, ethanol, isopropanol, n-butanol, glycols, e.g., ethylene glycol, ether, e.g., diethyl or diisopropyl ether, THF, dioxane, aliphatic hydrocarbons, e.g., petroleum ether, hexane, or aromatic hydrocarbon, e.g., benzene, toluene, xylene, halogenated hydrocarbons, e.g., chloroform, chlorobenzene, nitriles, e.g., acetonitrile, amides, e.g., DMF, dimethylacetamide, HMPA, sulfoxides, e.g., dimethyl sulfoxide, or mixtures of these solvents. The cyclization is normally carried out at temperatures of 0° to 300°, preferably from room temperature to the boiling point of the solvent employed, which temperature can optionally be elevated by the use of pressure (up to 200 atmospheres). The selection of the catalyst depends on the type of compound $HX_1$ to be split off. For example, when $X_1$ = halogen, basic catalysts are preferred, for example inorganic bases, e.g., alkali metal or alkaline earth metal hydroxides, carbonates or alcoholates, e.g., NaOH, KOH, LiOH, $Ba(OH)_2$, $Ca(OH)_2$, $Na_2CO_3$, $K_2CO_3$, $Li_2CO_3$, $NaOCH_3$, $KOCH_3$, $NaOC_2H_5$, $KOC_2H_5$, potassium tert.-butylate, or organic bases, e.g., tertiary amines, for example, triethylamine, pyridine, picolines and quinoline. In contrast thereto, when $X_1$ = OH, alkoxy, acyloxy, alkylsulfonyloxy or arylsulfonyloxy, acidic catalysts are advantageous, for example, inorganic acids, e.g., sulfuric acid, polyphosphoric acid, hydrobromic acid, hydrochloric acid and/or organic acids, e.g., formic, acetic, propionic or p-toluenesulfonic acid, which simultaneously can serve, if used in an excess, as the solvent. Normally, more vigorous conditions are required for the cyclization of these compounds. Compounds of Formula IV wherein $X_1$ = $NH_2$ split off ammonia during heating, for example during melting, thus forming the desired compounds of Formula I. A preferred mode of operation resides in producing the compounds of Formula IV in the nascent state in the presence or absence of an additional solvent (for example from a compound of Formula VI) and, rather than isolating them, cyclizing them directly to compounds of Formula I.

The diphenoxyacetic acid derivatives I can also be obtained by solvolysis (preferably hydrolysis) of other diphenoxyacetic acid derivatives of Formula V. In these derivatives, Z preferably is one of the following groups (wherein the groups R' and R" to be split off can be residues of any desired type and represent, for example, respectively alkyl of preferably 1-4 carbon atoms, wherein they can be identical or different and can also together be, for example, tetramethylene or pentamethylene, optionally interrupted by O): $CHal_3$; COOR''' (wherein R''' is different from $R_1$, especially alkyl of 5-12 carbon atoms or substituted alkyl; $C(OR')_3$; COOAcyl wherein Acyl is the acyl radical of a carboxylic acid of up to 25 carbon atoms, preferably the acyl radical of a corresponding diphenoxyacetic acid (I), i.e., having the formula:

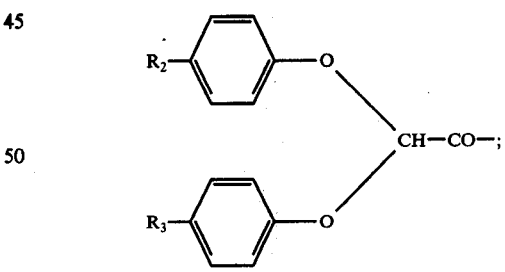

CN; $CONH_2$; CONHR'; CONR'R"; CONHOH; C(OH)=NOH; $CONHNH_2$; $CON_3$; C(OR')=NH; $C(NH_2)=NNH_2$; $C(NHNH_2)=NH$; CSOH; COSH; CSOR'; $CSNH_2$; CSNHR'; or CSNR'R". Preferably, Z is a nitrile or acid amide group. The compounds of Formula V are obtained, for example, by reacting the phenols IIa or IIb with compounds otherwise corresponding to Formula IIIa or IIIb, respectively, but having a Z group instead of $COOR_1$, in accordance with the above-described methods.

Hydrolysis of compounds of Formula V can be effected in an acidic or alkaline medium at temperatures of about −20° to 300°, preferably at the boiling temperature of the selected solvent. Suitable acidic catalysts are, for instance, mineral acids, e.g., hydrochloric, sulfuric, phosphoric and hydrobromic acid; suitable basic catalysts are inorganic soluble hydroxides and carbonates, e.g., sodium, potassium and calcium hydroxide and sodium and potassium carbonate. As solvent, preferred are water; lower alcohols, e.g., methanol or ethanol; ethers, e.g., THF or dioxane; amides, e.g., DMF; nitriles, e.g., acetonitrile; sulfones, e.g., tetramethylenesulfone; or mixtures of these solvents, especially water-containing mixtures. The preferred hydrolysis of nitriles (V, Z = CN) or acid amides (V, Z = $CONH_2$, CONHR' or CONR'R") is advantageously accomplished in an acidic medium, e.g., with acetic acid/hydrochloric acid, or in an alkaline medium, e.g., with alcoholic alkali.

It is also possible, by solvolytic methods, to produce esters of Formula I wherein $R_1$ = alkyl of 1-4 carbon atoms. For example, the nitriles V (Z = CN) can be converted, by reaction with alcoholic hydrochloric acid, into the corresponding iminoalkyl ether hydrochlorides, and the latter can be converted by partial hydrolysis into the corresponding alkyl esters.

If desired, the $R_1$ group of a thus-obtained compound of Formula I can be converted into another $R_1$ group according to methods described in the literature, e.g., by esterification, interesterification or solvolysis.

For example, it is possible to esterify a thus-produced acid of Formula I ($R_1$ = H) with an alkanol containing 1-4 carbon atoms, suitably in the presence of an inorganic or organic acid, e.g., HCl, HBr, HI, $H_2SO_4$, $H_3PO_4$, trifluoroacetic acid, benzenesulfonic acid or p-toluenesulfonic acid, or in the presence of an acidic ion exchanger, optionally with an inert solvent, e.g., benzene, toluene or xylene, at temperatures of from 0° to preferably the boiling point. The alcohol is preferably used in excess. The esters can also be obtained by chemical addition of the carboxylic acids I ($R_1$ = H) to olefins, e.g., isobutylene, or by reacting the carboxylic acids with diazoalkanes, e.g., diazomethane. Furthermore, the esters can be prepared by reacting metallic salts of the acids I ($R_1$ = H), preferably the alkali metal, lead or silver salts, with alkyl halides or with alkyl chlorosulfites, wherein the thus-obtained adducts are subsequently thermally decomposed. The esterification can also be effected in several stages. For example, it is possible first to produce, from an acid of Formula I ($R_1$ = H), the corresponding acid halogenide, e.g., the acid chloride, and to react the latter with the alcohol, optionally in the presence of an acidic or basic catalyst.

Furthermore, esters of Formula I ($R_1$ = alkyl of 1-4 carbon atoms) can be obtained by interesterification, especially by the reaction of other esters with an excess of the respective alcohol, or by reacting the carboxylic acids I ($R_1$ = H) with any desired other esters of the respective alcohol (preferably alkanoates, wherein the alkanoyl group has up to 4 carbon atoms), especially in the presence of a basic or acidic catalyst, e.g., sodium ethylate or sulfuric acid, and at a temperature of from 0° to preferably the boiling temperature of the reaction mixture.

It is also possible to convert the $R_1$ group in a thus-obtained compound fo Formula I into another $R_1$ group by treatment with a solvolyzing agent. In particular, a thus-obtained ester can be saponified to the corresponding acid I ($R_1$ = H). The solvolysis or saponification can be conducted according to one of the methods indicated above for the solvolysis of compounds of Formula V.

Preferably, the esters are saponified by treatment with alcoholic alkali solutions, e.g., ethanolic potassium hydroxide, at a temperature of from about 20° to 120°, preferably at the boiling temperature of the reaction mixture.

A basic compound of Formula I can be converted into the associated acid addition salt with the use of an acid. Suitable for this reaction are those acids forming physiologically acceptable salts. Thus, organic and inorganic acids are suitable, e.g., aliphatic, alicyclic, araliphatic, aromatic or heterocyclic mono- or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartric acid, malic acid, aminocarboxylic acids, sulfamic acid, benzoic acid, salicylic acid, phenylpropionic acid, citric acid, gluconic acid, ascorbic acid, nicotinic acid, isonicotinic acid, methanesulfonic acid, ethanedisulfonic acid, 2-hydroxyethanesulfonic acid, p-toluenesulfonic acid, naphthalene-mono- and -disulfonic acids, sulfuric acid, nitric acid, hydrohalic acids, such as hydrochloric acid or hydrobromic acid, or phosphoric acids, such as orthophosphoric acid.

The free acids of Formula I ($R_1$ = H) can be converted into physiologically acceptable metal and ammonium salts thereof by reaction with a base. Suitable salts are especially the sodium, potassium, magnesium, calcium and ammonium salts, including substituted ammonium salts, such as, for example, the dimethyl-, diethyl- and diisopropylammonium, monoethanol-, diethanol- and triethanolammonium, cyclohexylammonium, dicyclohexylammonium and dibenzylethylenediammonium salts.

Conversely, compounds of Formula I can be liberated from the acid addition salts thereof by treatment with strong bases and/or from the metal and ammonium salts thereof by treatment with acids.

The compounds of Formula I contain a center of asymmetry and are ordinarily present in the racemic form. The racemates can be separated into the optical antipodes thereof employing conventional methods known in the literature, for example by reaction with optically actives bases or acids. It is also possible to obtain optically active compounds in accordance with the described methods by using a starting compound which is optically active.

The compounds of Formula I and the physiologically acceptable salts thereof can be utilized in a mixture with solid, liquid and/or semiliquid excipients as medicinal agents in the human or veterinary medicine. Suitable carriers are those organic or inorganic substances suitable for parenteral, enteral or topical application and which do not react with the novel compounds, such as, for example, water, vegetable oils, benzyl alcohols, polyethylene glycols, gelatin, lactose, amylose, magnesium stearate, talc, vaseline, cholesterol. Suitable for parenteral application are especially solutions, preferably oily or aqueous solutions, as well as suspensions, emulsions or implants. For enteral application, advantageous are tablets, dragees, capsules, syrups, elixirs or suppositories, and for topical application, ointments, creams or powders. The above-mentioned preparations can optionally be sterilized or can contain auxiliary agents, such as lubricants, preservatives, stabilizers or wetting agents, emulsifiers, salts for influencing the osmotic pressure, buffers, coloring, flavoring and/or aromatic substances.

The novel compounds of Formula I and the physiologically acceptable salts thereof are normally administered analogously to the conventional compound clofibrate, preferably in dosages of between 10 and 1,000 mg., especially between 20 and 500 mg. per dosage unit. The daily dose is preferably between 0.5 and 20 mg./kg. of body weight. Oral administration is preferred.

The temperatures herein are indicated in degrees Celsius. In the following examples, "working up as usual" means the reaction mixture is cooled, concentrated by evaporation, water is added, the mixture is extracted with ether, the ether solution is washed with sodium bicarbonate solution and with water, dried over $Na_2SO_4$, the ether is distilled therefrom, and the crude product is purified by distillation or crystallization, optionally by the crystallization of an acid addition salt.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. 2.3 g. of sodium is dissolved in 200 ml. of absolute ethanol. The mixture is combined, under agitation, with 25.3 g. of 4-(4-piperidinophenyl)-phenol and then with 29.4 g. of the ethyl ester of α-bromo- α-(4-chlorophenoxy)-acetic acid, and the mixture is refluxed for 5 hours. Thereafter, the reaction mixture is cooled, filtered, washed with water, and the product is the ethyl ester of (4-chlorophenoxy)-[4-(4-piperidinophenyl)-phenoxy]-acetic acid, m.p. 107°–108° (from ethyl acetate/hexane).

Analogously, with the use of the following starting compounds:
  4-piperidinophenol
  4-(1,2,3,4-tetrahydroquinolino)-phenol
  4-(1,2,3,4-tetrahydro-4-quinolyl)-phenol
  4-(1-methyl-1,2,3,4-tetrahydro-4-quinolyl)-phenol
  4-(4-oxo-1,2,3,4-tetrahydroquinolino)-phenol
  4-(4-chromanyl)-phenol
  4-(4-thiochromanyl)-phenol
  4-(4-chlorophenoxy)-phenol,
the following final products can be obtained:
  the ethyl ester of each of the acids set forth below:
  (4-chlorophenoxy)-(4-piperidinophenoxy)-acetic acid
  (4-chlorophenoxy)-[4-(1,2,3,4-tetrahydroquinolino)-phenoxy]-acetic acid
  (4-chlorophenoxy)-[4-(1,2,3,4-tetrahydro-4-quinolyl)-phenoxy]-acetic acid
  (4-chlorophenoxy)-[4-(1-methyl-1,2,3,4-tetrahydro-4-quinolyl)-phenoxy]-acetic acid, oil; $n_D^{20}$ 1.5700
  (4-chlorophenoxy)-[4-(4-oxo-1,2,3,4-tetrahydroquinolino)-phenoxy]-acetic acid, m.p. of this ethyl ester: 122°–123°;
  (4-chorophenoxy)-[4-(4-chromanyl)-phenoxy]-acetic acid, oil; $n_D^{20}$ 1.5808;
  (4-chlorophenoxy)-[4-(4-thiochromanyl)-phenoxy]-acetic acid
  (4-chlorophenoxy)-[4-(4-chlorophenoxy)-phenoxy]-acetic acid, oil; $n_D^{20}$ 1.5796.

b. 4.64 g. of the ethyl ester of (4-chlorophenoxy)-[4-(4-piperidinophenyl)-phenoxy]-acetic acid is refluxed with 1 g. of KOH in 25 ml. of ethanol for 2½ hours. The mixture is then evaporated, combined with water, washed with ether, and hydrochloric acid is added to pH 5. The thus-obtained (4-chlorophenoxy)-[4-(4-piperidinophenyl)-phenoxy]-acetic acid is filtered off.

Analogously, the following final compounds are obtained by saponification of the corresponding ethyl esters:
  (4-chlorophenoxy)-(4-piperidinophenoxy)-acetic acid, diisopropylamine salt, m.p. 148°–150°;
  (4-chlorophenoxy)-[4-(1,2,3,4-tetrahydroquinolino)-phenoxy]-acetic acid, diisopropylamine salt, m.p. 129°–132°;
  (4-chlorophenoxy)-[4-(1,2,3,4-tetrahydro-4-quinolyl)-phenoxy]-acetic acid;
  (4-chlorophenoxy)-[4-(1-methyl-1,2,3,4-tetrahydro-4-quinolyl)-phenoxy]-acetic acid,, diisopropylamine salt, m.p. 152°–155°;
  (4-chlorophenoxy)-[4-(4-oxo-1,2,3,4-tetrahydroquinolino)-phenoxy]-acetic acid;
  (4-chlorophenoxy)-[4-(4-chromanyl)-phenoxy]-acetic acid;
  (4-chorophenoxy)-[4-(4-thiochromanyl)-phenoxy]-acetic acid;
  (4-chlorophenoxy)-[4-(4-chlorophenoxy)-phenoxy]-acetic acid, m.p. 122°–123°; cyclohexylamine salt, m.p. 130°.

EXAMPLE 2 a. 17.7 g. of 4-piperidinophenol is added to a suspension of 2.4 g. of NaH in 200 ml. of dimethylacetamide. The mixture is agitated for one hour at 20°, heated to 100°, and then 25.9 g. of the ethyl ester of α-bromo-α-phenoxyacetic acid is added thereto. The mixture is heated for 16 hours to 160°, worked up as usual, and the thus-obtained product is phenoxy-(4-piperidinophenoxy)-acetic acid ethyl ester.

Analogously, the following final products are obtained with the aid of the corresponding phenols:
  phenoxy-[4-(4-piperidinophenyl)-phenoxy]-acetic acid ethyl ester
  phenoxy-[4-(1,2,3,4-tetrahydroquinolino)-phenoxy]-acetic acid ethyl ester
  phenoxy-[4-(1,2,3,4-tetrahydro-4-quinolyl)-phenoxy]-acetic acid ethyl ester
  phenoxy-[4-(1-methyl-1,2,3,4-tetrahydro-4-quinolyl)-phenoxy]-acetic acid ethyl ester
  phenoxy-[4-(4-oxo-1,2,3,4-tetrahydroquinolino)-phenoxy]-acetic acid ethyl ester
  phenoxy-[4-(4-chromanyl)-phenoxy]-acetic acid ethyl ester
  phenoxy-[4-(4-thiochromanyl)-phenoxy]-acetic acid ethyl ester
  phenoxy-[4-(4-chlorophenoxy)-phenoxy]-acetic acid ethyl ester b. 3.55 g. of ethyl phenoxy-(4-piperidinophenoxy)-acetate is refluxed with 1 g. of NaOH in 40 ml. of methanol for 4 hours. The mixture is concentrated by evaporation, mixed with water, washed with ether, hydrochloric acid is added thereto to a pH of 5, and phenoxy-(4-piperidinophenoxy)-acetic acid is thus obtained.

Analogously, the following final compounds are produced by saponification of the corresponding ethyl esters:
  phenoxy-[4-(4-piperidinophenyl)-phenoxy]-acetic acid
  phenoxy-[4-(1,2,3,4-tetrahydroquinolino)-phenoxy]-acetic acid
  phenoxy-[4-(1,2,3,4-tetrahydro-4-quinolyl)-phenoxy]-acetic acid phenoxy-[4-(1-methyl-1,2,3,4-tetrahydro-4-quinolyl)-phenoxy]-acetic acid
phenoxy-[4-(4-oxo-1,2,3,4-tetrahydroquinolino)-phenoxy]-acetic acid
phenoxy-[4-(4-chromanyl)-phenoxy]-acetic acid
phenoxy-[4-(4-thiochromanyl)-phenoxy]-acetic acid
phenoxy-[4-(4-chlorophenoxy)-phenoxy]-acetic acid.

EXAMPLE 3

A mixture of 1.29 g. of 4-chlorophenol and 0.23 g. of sodium in 60 ml. of xylene is refluxed for 3 hours. The mixture is cooled to 20°, and 3.9 g. of ethyl α-bromo-α-[4-(1,2,3,4-tetrahydroquinolino)-phenoxy]-acetate in 30 ml. of xylene is added thereto; the suspension is stirred for 6 hours under boiling heat, cooled off, and treated with 2 ml. of ethanol. The inorganic precipitate is filtered off, the filtrate is concentrated by evaporation, the residue is taken up in ether, the solution is washed with $NaHCO_3$ solution and saturated NaCl solution, dried over $MgSO_4$, and evaporated, thus obtaining (4-chloro-phenoxy)-[4-(1,2,3,4-tetrahydroquinolino)-phenoxy]-acetic acid ethyl ester.

Analogously, using the phenols set forth in Example 1 and reacting same with the following compounds:
the methyl ester
n-propyl ester
isopropyl ester
n-butyl ester
isobutyl ester
sec.-butyl ester
tert.-butyl ester
of α-bromo-α-(4-chlorophenoxy)-acetic acid,
the corresponding esters of the acids set forth in Example 1(b) are obtained, for example:
the methyl ester
n-propyl ester
isopropyl ester
n-butyl ester
isobutyl ester
sec.-butyl ester
tert.-butyl ester
of (4-chlorophenoxy)-[4-(1,2,3,4-tetrahydroquinolino)-phenoxy]-acetic acid.

EXAMPLE 4

A solution of 23.9 g. of α-chloro-α-(4-chlorophenoxy)-acetic acid ethyl ester present in 60 ml. of acetone is gradually added to an agitated mixture of 23.9 g. of 4-(4-oxo-1,2,3,4-tetrahydroquinolino)-phenol, 6.9 g. of $K_2CO_3$, and 80 ml. of acetone. The mixture is refluxed under agitation for 12 hours, filtered, and worked up as usual, thus obtaining (4-chlorophenoxy)-[4-(4-oxo-1,2,3,4-tetrahydroquinolino)-phenoxy]-acetic acid ethyl ester, m.p. 122°–123°.

EXAMPLE 5

A mixture of 22 g. of 4-(4-chlorophenoxy)-phenol and 23 g. of the ethyl ester of 4-chlorophenoxyglycolic acid (obtainable by the selective hydrolysis of 4-chlorophenoxybromoacetic acid ethyl ester with water) is combined with 15 g. of sulfuric acid, and the reaction mixture is agitated for 2 hours at 50°–60°. After cooling, the mixture is combined with water, diluted NaOH is added to pH 8, and the aqueous phase is extrated with ether. The mixture is then dried, evaporated, and the thus-obtained product is (4-chlorophenoxy)-[4-(4-chlorophenoxy)-phenoxy]-acetic acid ethyl ester, oil, $n_D^{20}$ 1.5796.

EXAMPLE 6 a. 17.7 g. of 4-piperdinophenol is dissolved in 100 ml. of acetone. Under agitation, 4 g. of NaOH is added thereto, and then the mixture is combined with 26.5 g. of α-bromo- α -(4-chlorophenoxy)-acetic acid in 60 ml. of acetone by adding the latter solution dropwise under agitation nd refluxing. The mixture is stirred for another hour at 56° and allowed to stand for 24 hours. The acetone is distilled off, the residue is dissolved in 1 liter of water, the solution is repeatedly washed with ether and acidified with HCl to pH 5. The thus-precipitated (4-chlorophenoxy)-(4-piperdinophenoxy)-acetic acid is converted into the diisopropylamine salt (m.p. 148°–150°).

Analogously, the acids indicated in Examples 1(b) and 2(b), respectively, are obtained from the phenols set forth in Example 1(a).

b. One gram of (4-chlorophenoxy)-(4-piperidinophenoxy)-acetic acid is dissolved in 20 ml. of ether and mixed dropwise with ethereal diazomethane solution until the mixture assumes a permanent yellow coloring. After evaporation, the methyl ester of (4-chlorophenoxy)-(4-piperidinophenoxy)-acetic acid is obtained.

Analogously, the corresponding methyl esters are produced from the remaining acids listed in Examples 1(b) and 2(b), respectively.

c. Five grams of (4-chlorophenoxy)-(4-piperidinophenoxy)-acetic acid is dissolved in 200 ml. of saturated ethanolic hydrochloric acid; the mixture is allowed to stand for 12 hours at room temperature, refluxed for 2 hours, and evaporated. The residue is dissolved in water, the aqueous solution is adjusted to pH 8 with 1N NaOH, and the mixture is extracted with ethyl acetate. After drying and evaporation, the ethyl ester of (4-chlorophenoxy)-(4-piperidinophenoxy)-acetic acid is obtained.

Analogously, the corresponding ethyl esters set forth in Examples 1(a) and 2(a), respectively, are produced from the acids indicated in Examples 1(b) and 2(b), respectively with the use of ethanolic hydrochloric acid. If other alcohols are employed in place of ethanol, the corresponding esters are obtained, for example, with n-butanol, the n-butyl ester of (4-chlorophenoxy)-(4-piperidinophenoxy)-acetic acid is formed.

EXAMPLE 7

2.3 g. of 1,5-dibromopentane, 3.2 g. of (4-chlorophenoxy)-(4-aminophenoxy)-acetic acid ethyl ester [obtainable by reacting Na-4-nitrophenolate with α-bromo-α-(4-chlorophenoxy)-acetic acid ethyl ester to obain the ethyl ester of (4-chlorophenoxy)-(4-nitrophenoxy)-acetic acid and subsequent hydrogenation], and 1.4 g. of $K_2CO_3$ are refluxed for 12 hours in 40 ml. of n-butanol. As an intermediate compound, the ethyl ester of (4-chlorophenoxy)-[4-(5-bromopentylamino)-phenoxy]-acetic acid is produced. After working up the mixture as usual, (4-chlorohenoxy)-(4-piperidinophenoxy)-acetic acid ethyl ester is obtained.

Analogously, ethyl (4-chlorophenoxy)-[4-(4-piperidinophenyl)-phenoxy]-acetate, m.p. 107°–108°, is produced from ethyl (4-chlorophenoxy)-[4-(p-5-bromopentylaminophenyl)-phenoxyl]-acetate.

EXAMPLE 8

Two grams of (4-chlorophenoxy)-[4-(4-chlorophenoxy)-pheonxy]-acetonitrile [obtainable from 4-(4-chlorophenoxy)-phenol and α-bromo-α-4-chlorophenoxyacetonitrile] is refluxed with 2 g. of KOH in 20 ml. of ethanol and 2 ml. of water for 40 hours. The mixture is then evaporated, combined with water, extracted with ether, and hydrochloric acid is added to pH 5, thus obtaining (4-chlorophenoxy)-[4-(4-chlorophenoxy)-phenoxy]-acetic acid.

Analogously, the carboxylic acids set forth in Examples 1(b) and 2(b), respectively, are produced by alkaline hydrolysis of the corresponding nitriles.

EXAMPLE 9

One gram of (4-chlorophenoxy)-[4-(1,2,3,4-tetrahydroquinolino)-phenoxy]-aceytonitrile is refluxed with 6 ml. of acetic acid and 6 ml. of concentrated hydrochloric acid for 2 hours under nitrogen. The mixture is then evaporated, dissolved in dilute NaOH, extracted with ether, and hydrochloric acid is added to pH 5, thus producing (4-chlorophenoxy)-[4-(1,2,3,4-tetrahydroquinolino)-phenoxy]-acetic acid; diisopropylamine salt, m.p. 129°–132°.

Analogously, the carboxylic acids set forth in Examples 1(b) and 2(b), respectively, are obtained by acidic hydrolysis of the corresponding nitriles.

EXAMPLE 10

Three grams of (4-chlorophenoxy)-[4-(1,2,3,4-tetrahydroquinolino)-phenoxy]-acetamide [obtainable from 4-(1,2,3,4-tetrahydroquinolino)-phenol and α-bromo-α-(4-chlorophenoxy)-acetamide] and 5 g. of KOH are refluxed in 100 ml of ethanol for 3 hours under nitrogen. The mixture is evaporated, combined with water, extracted with ether, and hydrochloric acid is added to pH 4, thus obtaining (4-chlorophenoxy)-[4-(1,2,3,4-tetrahydroquinolino)-phenoxy]-acetic acid; diisopropylamine salt, m.p. 129°–132°.

Analogously, the carboxylic acids set forth in Examples 1(b) and 2(b), respectively, are produced by alkaline hydrolysis of the corresponding amides.

EXAMPLE 11

10 g. of (4-chlorophenoxy)-[4-(1,2,3,4-tetrahydroquinolino)-phenoxy]-acetyl chloride (obtainable from the acid and SOCl₂) is heated with 100 ml. of absolute n-propanol for 3 hours to 95°. The mixture is then evaporated, the residue is mixed with dilute solution of sodium hydroxide, and the aqueous solution is extracted with ether. The ether solution is washed twice with dilute NaOH and twice with water, then dried, and the ether is removed by evaporation, thus producing (4-chlorophenoxy)-[4-(1,2,3,4-tetrahydroquinolino)-phenoxy]-acetic acid n-propyl ester.

The following examples relate to pharmaceutical preparations containing active agents of general Formula I and/or the physiologically acceptable salts thereof:

EXAMPLE A

Tablets

A mixture of 10 kg. of the diisopropylamine salt of (4-chlorophenoxy)-[4-(1-methyl-1,2,3,4-tetrahydro-4-quinolyl)-phenoxy]-acetic acid, 40 kg. of lactose, 12 kg. of wheat starch, 2 kg. of talc, and 1 kg. of magnesium stearate is compressed to tablets in the usual manner, so that each tablet contains 100 mg. of the active agent.

EXAMPLE B

Dragees

Analogously to Example A, dragee cores are pressed which are then provided with a coating consisting of sugar, corn starch, talc, and tragacanth in the usual manner.

In analogy to the above, tablets and dragees can be obtained containing one or more of the other effective agents of Formula I and/or the physiologically acceptance salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

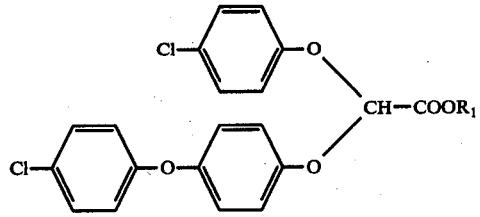

wherein R₁ is H or alkyl of 1–4 carbon atoms, or when R₁ is H, a physiologically acceptable salt thereof.

2. A compound of claim 1 wherein R₁ is alkyl of 1–4 carbon atoms.

3. A physiologically acceptable salt of claim 1.

4. A compound of claim 1, (4-chlorophenoxy)-[4-(4-chlorophenoxy)-phenoxy]-acetic acid.

5. A compound of claim 1, (4-chlorophenoxy)-[4-(4-chlorophenoxy)-phenoxy]-acetic acid ethyl ester.

* * * * *